(12) United States Patent
Parkin et al.

(10) Patent No.: US 6,503,256 B2
(45) Date of Patent: Jan. 7, 2003

(54) MICRODERM ABRASION DEVICE AND METHOD

(75) Inventors: Roger Parkin, Newtown Square, PA (US); George Maguire, W. Conshohocken, PA (US); Young Cho, Cherry Hill, NJ (US)

(73) Assignee: Dermamed, Inc., Lenni, PA (US)

( * ) Notice: Subject to any disclaimer, the term of this patent is extended or adjusted under 35 U.S.C. 154(b) by 0 days.

(21) Appl. No.: 09/805,700

(22) Filed: Mar. 13, 2001

(65) Prior Publication Data

US 2002/0133176 A1 Sep. 19, 2002

(51) Int. Cl.[7] .............................................. A61B 17/50
(52) U.S. Cl. .......................... 606/131; 451/87; 451/90; 451/99; 604/290
(58) Field of Search .......................... 606/131; 604/289, 604/290, 22; 451/87, 99, 102, 90

(56) References Cited

U.S. PATENT DOCUMENTS

| | | | | |
|---|---|---|---|---|
| 3,815,286 A | * | 6/1974 | Piet .............................. | 451/90 |
| 5,037,431 A | * | 8/1991 | Summers et al. ............. | 604/22 |
| 6,183,148 B1 | * | 2/2001 | Chang ........................ | 606/131 |
| 6,193,589 B1 | * | 2/2001 | Khalaj ........................ | 451/102 |
| 6,235,039 B1 | * | 5/2001 | Parkin et al. ................ | 606/131 |
| 6,238,275 B1 | * | 5/2001 | Metcalf et al. ............. | 451/101 |
| 6,322,568 B1 | * | 11/2001 | Bernabei et al. ............ | 606/131 |

FOREIGN PATENT DOCUMENTS

JP          3-267053     * 11/1991

* cited by examiner

Primary Examiner—Rodney M. Lindsey
(74) Attorney, Agent, or Firm—Ostrolenk, Faber, Gerb & Soffen, LLP

(57) ABSTRACT

A micro-dermabrasion system and method in which a handpiece includes an axially aligned treatment orifice and laterally offset particle supply and waste removal channels. At least a portion of the particle supply channel is angularly offset relative to the waste removal channel so the particle stream impinges substantially on the center of the treatment orifice. The handpiece employs tapered couplers to permit easy attachment and detachment of particle supply and waste removal lines in a handpiece having a small diameter. The particle supply container is designed to be pre-filled by a supplier, and disposed of when empty without disassembly. The supply container is also constructed to permit controlled aeration of the particles before delivery to the handpiece to reduce clogging of the particle lines and to facilitate continuous adjustment of particle flow rate.

57 Claims, 8 Drawing Sheets

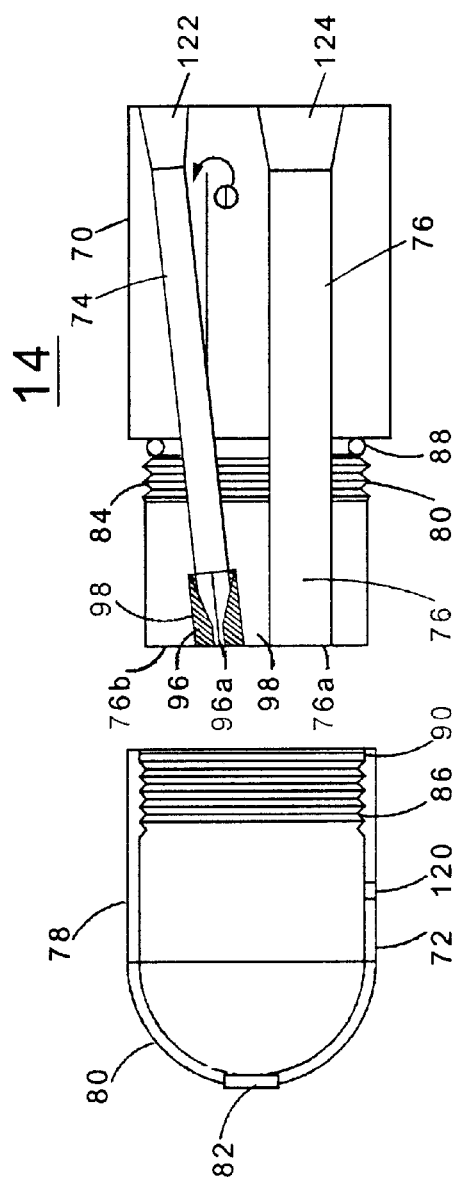
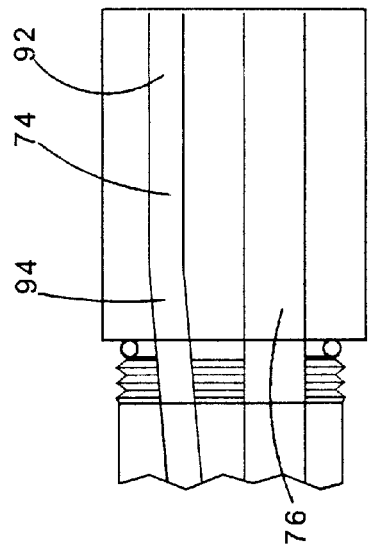
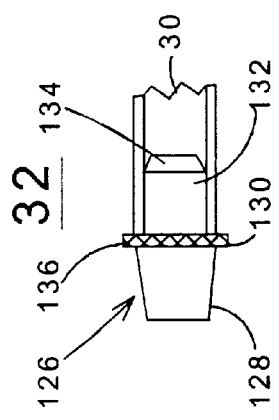
FIG. 3
FIG. 4
FIG. 5

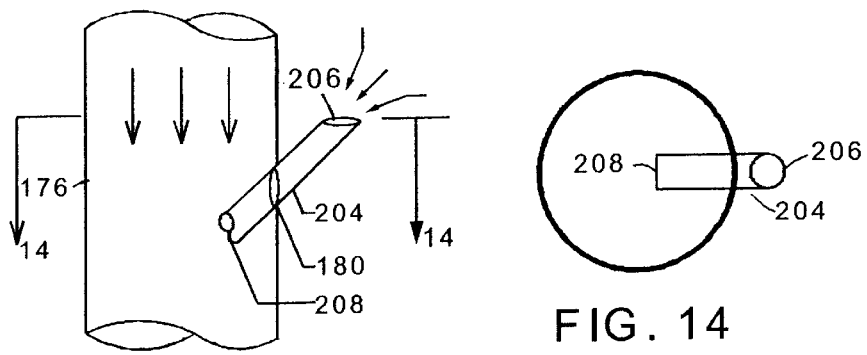
FIG. 13
FIG. 14
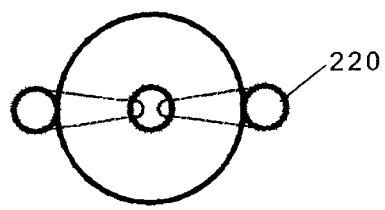
FIG. 16
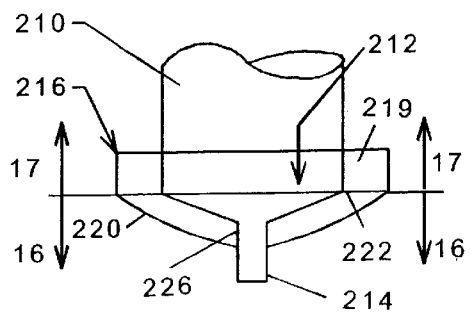
FIG. 15
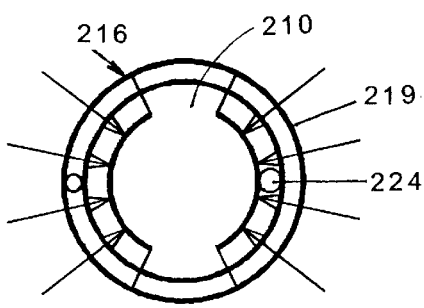
FIG. 17

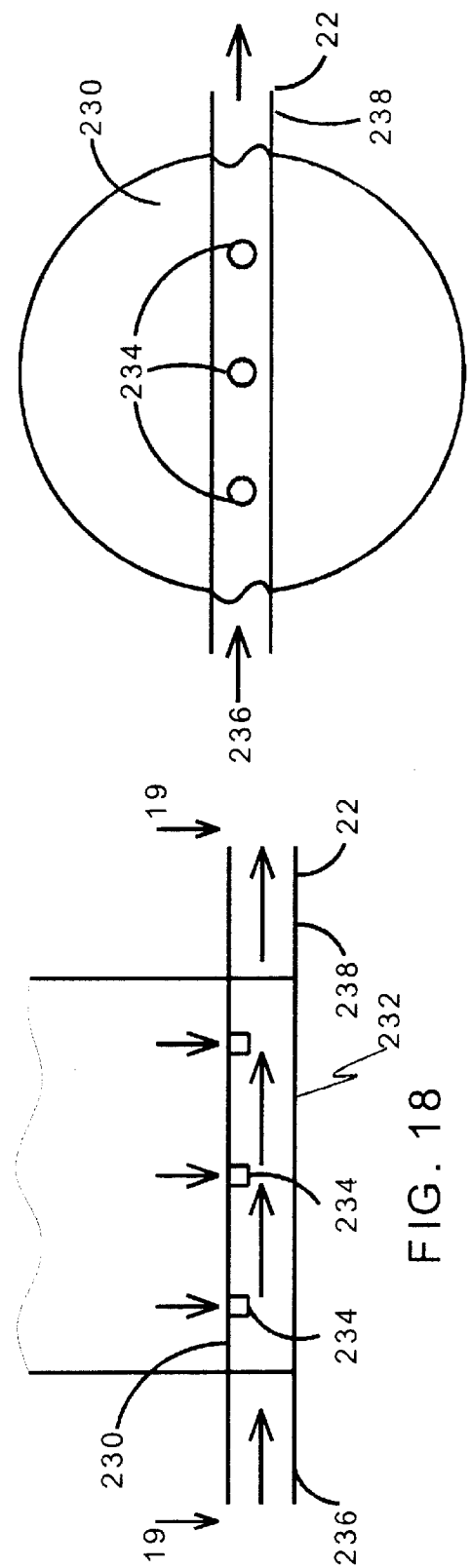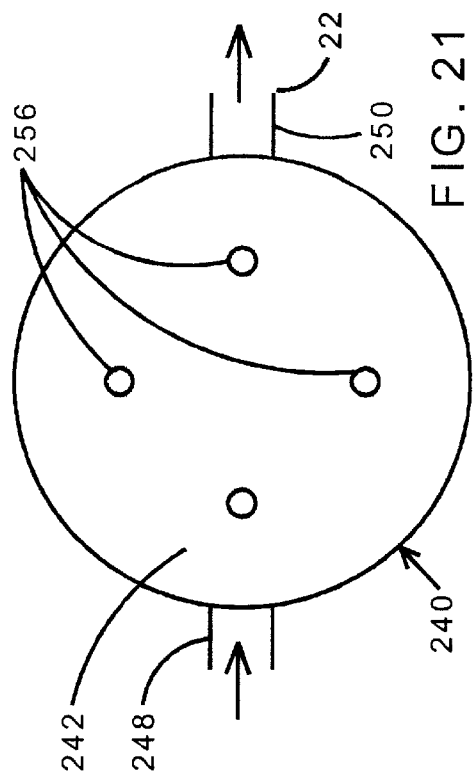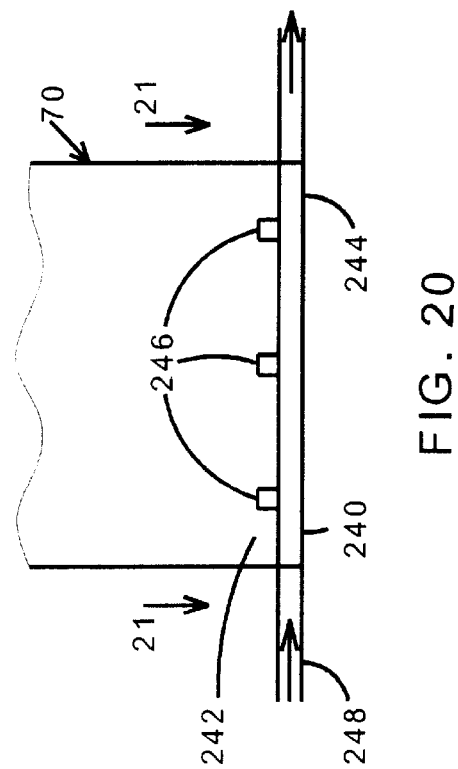

MICRODERM ABRASION DEVICE AND METHOD

RELATED APPLICATIONS

This application relates to subject matter disclosed application Ser. No. 09/255,954, filed Feb. 23, 1999, entitled, SKIN ABRASION DEVICE now U.S. Pat. No. 6,432,113 and application Ser. No. 09/496,394, filed Feb. 2, 2000, entitled, SKIN ABRASION DEVICE now U.S. Pat. No. 6,235,039, the contents of which are both incorporated by reference herein.

FIELD OF THE INVENTION

This invention relates to the removal of surface portions of dead or living tissue, sometimes termed microdermal abrasion or micro-dermabrasion. More particularly, the invention relates to an improved apparatus and process for the abrasion of surface portions of human tissue by the controlled flow of abrasive particles.

BACKGROUND OF THE INVENTION

Conventional microdermal abrasion apparatuses employ a stream of abrasive particles such as sand applied to the surface of the tissue or skin by means of a vacuum pump through an opening in a hand held tool (termed a handpiece) which is sealed against the skin. The handpiece is passed over the area of skin to be abraded so the particle stream can impinge on the skin through an opening in the handpiece. The spent particles and the removed tissue are then collected by vacuum pressure in the handpiece and are delivered to a collection container for later disposal. Suitable filtration is provided to prevent the escape of the abraded tissue and particles into the vacuum pump and the atmosphere.

Conventional handpieces usually provide a first channel for conducting abrasive particles from a supply container to the area to be treated and a second channel for conducting the spent particles and abraded skin away from the area treated to the collection container.

A typical prior art microdermal abrasion device is shown in U.S. Pat. No. 5,037,432. The hand-held head disclosed in this patent is a long tubular structure including an inlet passage for the abrasive particles and an outlet passage for removal of the spent particles and abraded skin. A treatment orifice in the form of an off-center hole at a 45° angle to the longitudinal axis of the handpiece is aligned with the abrasive particle inlet passage to permit the abrasive particle to reach the area of skin to be treated.

The above described handpiece has several drawbacks. Because the treatment orifice is off-axis, the handpiece must be carefully positioned to assure proper contact with the area under treatment, and because it must be held at an angle, is difficult to manipulate over a curved surface such as a human face. As a consequence, the patented handpiece is both uncomfortable and tiring to use.

Moreover, the patented handpiece has been found to be subject to frequent clogging. This requires the operator to repeatedly stop the treatment to clear the blockage.

In addition, the handpiece described above includes a disposable tip or bell section which contains the treatment orifice. The tip is press-fitted onto the body of the handpiece and is tightly sealed thereto to prevent accidental escape of abraded skin and loss of vacuum. This makes it hard to remove for replacement. Further, with the treatment orifice positioned off the longitudinal axis, the tip must be carefully aligned with the particle inlet passage. Although an alignment key on the tip and a cooperating keyway on the handpiece body are provided, the need for proper alignment adds to the difficulty of removal and replacement.

As previously noted, prior art devices typically employ vacuum pumps as the source of operating power. However, the prior art (including the patented device described above) do not provide a convenient way for the suction to be changed by the operator when a weaker or more forceful stream of abrasive particles is desired at particular locations. Similarly, continuously variable control of particle flow rate, i.e., particle volume, has not been provided. Instead, only a single or a few predetermined flow rates are permitted. For example, U.S. Pat. No. 5,954,730, issued to Bernabei, provides a two-position switch operated valve allowing two levels of suction pressure.

In addition, in some conventional handpieces, the tubes leading from the particle supply container and to the collection container are formed integrally with or press-fitted onto the handpiece. This means that the handpiece must also be discarded when the tubes, which are subject to wear due to the effects of the abrasive particles flowing therein, are replaced. This construction also makes sterilization of the handpiece impractical, and sterility of only the replaceable tip can be assured.

In other known devices, threaded fittings are provided for connecting the handpiece to the tubes, such as disclosed in U.S. Pat. No. 5,037,432, issued to Molinari. In this device, however, the diameter of the handpiece is small for ease of handling. Therefore, a tool is required to manipulate the threaded connections, which is both inconvenient and time consuming. Also, the small size of the fittings dictates use of fine threads which have proved to be subject to crossthreading.

Yet a further problem with known prior art relates to the particle supply and waste containers. Typically, the containers are permanent parts of the apparatus so the supply container must be refilled when empty and the waste container must be emptied when full. When either of these operations are performed, clouds of fine abrasive dust are released.

In the case the supply container, this is an inconvenience in that the dust settles on surrounding surfaces and must be removed. Moreover, care must be taken to avoid abrasion when the surfaces are cleaned.

In the case of the waste container, however, the problem is more severe as the abraded skin particles are a source of potential biological contamination to which the operator is directly exposed when emptying the waste container. In addition, the dust cloud released when the container is emptied is a source of environmental contamination.

In one known device disclosed in U.S. Pat. 5,971,999 to Naldoni, a refilled supply container is employed which is then used as the waste container when it is empty. However, these containers are open while they are attached to and removed from the Naldoni machine, so the operator and the environment are still exposed to the clouds of abrasive particles.

In another known device shown in French Patent 2,712, 172 to Rabier, a filter bag inside a non disposable outer container is used for waste collection. The full bag is open when it is removed from the outer container, thus again exposing the operator and the environment to the contaminated waste. Also, during disposal, the operator and the environment will be exposed to any contaminated dust which escapes through the filter bag into the outer container.

Moreover, with all of the known devices, various nondisposable parts are permanently mounted on the machine. This makes it difficult, if not impossible, to clean these parts thoroughly.

Yet another problem in the prior art is non-uniform flow and clogging of the abrasive particles in the supply line and the passages of the handpiece. These problems are apparently related in a complex manner to the geometry of the flow passages, and are serious drawbacks in conventional equipment.

SUMMARY OF THE INVENTION

According to the present invention, a novel apparatus and process is provided which alleviates the problems with prior art devices as stated above, and which provides other operational improvements as well.

A first aspect of the invention is the provision of a novel handpiece having several important features.

As a first feature, the novel handpiece is comprised of an elongated body portion, a particle supply channel and a waste removal channel extending lengthwise through the body portion, and a removable tip which may be attached to one end of the body portion, A treatment orifice is provided at one end of the tip and is aligned with the longitudinal axis of the handpiece. The particle stream exits the particle supply channel at a point which is radially displaced from the longitudinal axis of the handpiece, but the particle supply channel is so oriented that the stream of abrasive particles is directed substantially toward the center of the treatment orifice. In a preferred embodiment, this is achieved by angularly offsetting the particle supply channel relative to the longitudinal axis of the handpiece.

A further feature of the novel handpiece is the employment of a coupler having internally tapered body portions which mate with externally tapered plug portions to connect the handpiece to the particle supply and waste removal lines. These couplers can be attached and detached simply by twisting the plug portion relative to the body portion, and their use eliminates the need for permanently secured tubes, couplers requiring tools for connection and disconnection or employment of fittings large enough to permit finger manipulation.

According to another feature of the handpiece of the present invention, the diameter of the waste removal channel in the handpiece is substantially larger than that of the particle supply.

According to a second aspect of the invention, a novel particle supply container is provided which controllably aerates the abrasive particles before delivery to the handpiece. In one such supply container, a mixing tube, open at the top, is positioned in the container with its top opening above the particle fill level. The bottom of the mixing tube is connected to a tube which feeds the handpiece particle supply channel. Air is introduced to the container through an inlet opening, and is drawn into the mixing tube by the suction in the system. An opening in the side of the mixing tube near the bottom admits particles under gravity feed, and the particles are mixed with the air stream before exiting the supply container into the particle feed tube. Fine control of the air-particle ratio is provided by a valve which permits additional air to enter the particle feed line just outside the container.

According to another container design, the top of the mixing tube extends through an opening in the top of the container. This eliminates the need for a separate air inlet. Pressure equalization above the level of the particles in the supply container is provided by an outlet hole near the top of the mixing tube.

According to a further container design, a separate air inlet tube is provided which enters the container at the bottom and delivers air through a top opening to the space above the stored particles. Air enters the top of the mixing tube and particles are gravity fed through a hole near the bottom as in the previously described designs.

In other designs, separate particle supply tubes are connected to the mixing tube, and in yet further variations, mixing chambers are provided at the bottom of the container in which the aeration process takes place.

Employment of controlled aeration not only alleviates clogging of the particle flow passages, but also improves the uniformity of particle flow, and permits continuous variable flow rate (particle volume) adjustment.

According to a third aspect of the invention, the particle supply container is designed to be pre-filled by a supplier, installed in a substantially sealed condition, and disposed of in a substantially sealed condition when it is empty. The waste receptacle which receives the spent particles and the abraded skin includes an internal filter also designed for disposal in a substantially sealed condition. This eliminates the need for the operator to refill the supply container and empty and clean the waste receptacle, and even of greater importance, prevents exposure of the operator and the environment to the abrasive particles and the removed skin.

As a fourth aspect of the present invention, there is provided an improved design for a microdermal abrasion apparatus in which an aerated stream of abrasive particles is transported from a pre-filled and disposable supply container having the various features and advantages described above, delivered through a supply tube to an inlet channel in a handpiece, and is delivered from the inlet channel to an axially positioned treatment orifice in a disposable tip at the end of the handpiece. The inlet channel in the handpiece is designed so that the stream of abrasive particles is directed substantially toward the center of the treatment orifice.

Air is evacuated from the tip by a vacuum source connected to a waste removal channel which extends through the handpiece. The spent abrasive particles and the abraded skin, are withdrawn by the suction and delivered through a waste removal line to a combined waste filter and disposal container (referred to below as a "disposable waste filter" or "waste filter").

The apparatus as described in this aspect of the invention avoids exposure to both clean and contaminated abrasive particles, functions substantially without clogging, provides convenient adjustment of the particle volume and application force, and allows comfortable and convenient use by the operator.

As still another aspect of the present invention there is provided an improved method for microdermal abrasion in which an aerated stream of abrasive particles is transported from a pre-filled and disposable supply container having the various features and advantages described above, delivered through a supply tube to an inlet channel in a handpiece, and is delivered from the inlet channel to an axially positioned treatment orifice in a disposable tip at the end of the handpiece. The incoming stream of abrasive particles is directed substantially toward the center of the treatment orifice.

Air is evacuated from the tip by a vacuum source connected to a waste removal channel which extends through the handpiece. The tip is placed against a surface of the skin to be abraded with the opening in the tip sealed against the skin. The spent abrasive particles and the abraded skin are withdrawn by the suction and delivered through a waste removal line to a disposable waste filter.

Other features of the invention, and advantages over the prior art will become apparent from consideration of the following detailed description in conjunction with the drawings.

BRIEF DESCRIPTION OF THE DRAWINGS

FIG. 3 is an exploded longitudinal sectional view of the handpiece shown in FIG. 2.

FIG. 4 is a fragmentary sectional view illustrating an alternative construction of the particle supply channel of the handpiece illustrated in FIG. 3.

FIG. 5 is a side elevation of a tapered handpiece coupler as described in the invention.

FIG. 13 is a fragmentary schematic side view of a modified aeration tube as described in the invention.

FIG. 14 is a cross-sectional view taken along line 14—14 in FIG. 13.

FIG. 15 is a fragmentary schematic side view of a fourth embodiment of the novel particle supply container as described in the invention.

FIG. 16 is a cross-sectional view taken along section line 16—16 in FIG. 15.

FIG. 17 is a cross-sectional view taken along section line 17—17 in FIG. 15.

FIG. 18 is a fragmentary side view of an aeration manifold as described in the invention.

FIG. 19 is a cross—sectional view taken along section line 19—19 in FIG. 18.

FIG. 20 is a schematic side elevation of an alternative construction of an aeration manifold as described in the invention.

FIG. 21 is a cross-sectional view taken along section line 21—21 in FIG. 20.

DETAILED DESCRIPTION OF THE INVENTION

Figure 1:
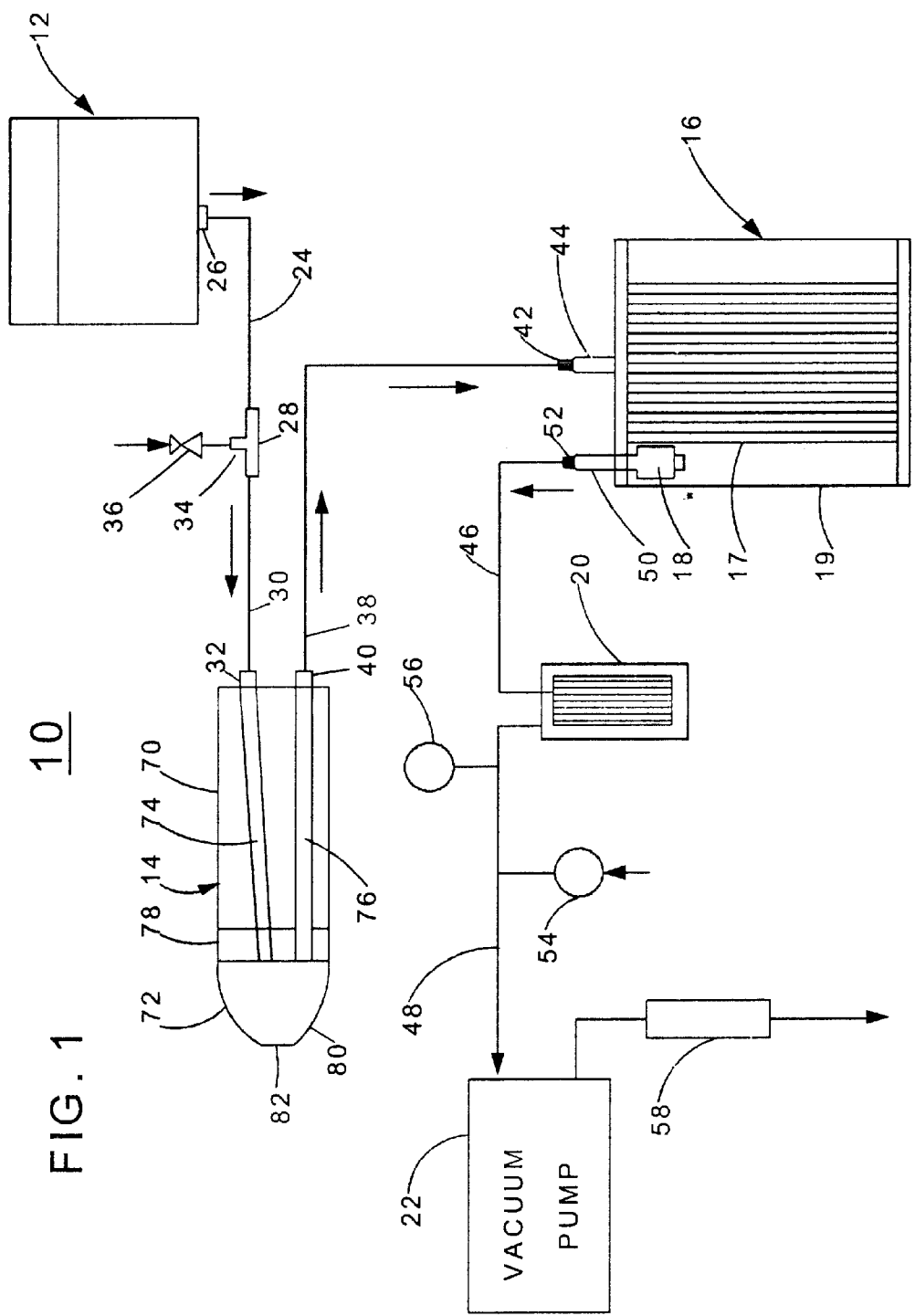
FIG. 1 is a schematic diagram of a novel microdermal abrasion system as described in the present invention.

Referring to the drawings, in which like reference numerals refer to like elements, there is shown in FIG. 1 a microdermal abrasion apparatus generally denoted at 10, comprised of an abrasive supply container 12, a handpiece 14, a disposable waste filter 16, an air line filter 20 and a vacuum pump 22. Waste filter 16 is comprised of a primary filter element 17, and a secondary filter element 18, both housed in a sealed outer container 19.

The particle supply path from container 12 to handpiece 14 is comprised of an outlet tube 24 connected to container 12 by an outlet coupler 26, a Tee-connector 28 and a particle supply line 30, the latter connected to handpiece 14 by an inlet coupler 32. The leg 34 of Tee-connector 28 is connected to an air supply valve 36, as described in more detail below.

A waste disposal line 38 connects handpiece 14 to waste filter 16. An outlet coupler 40 at one end of waste disposal line 38 connects to handpiece 14. The other end of waste disposal line 38 connects to an inlet line 44 on waste filter 16 by means of a suitable fitting 42.

Vacuum pump 22 provides the suction for delivery of abrasive particles to handpiece 14 and for waste removal. Waste filter 16 is connected to vacuum pump 22 in any convenient or desired manner, e.g., by a first air outlet line 46, air line filter 20 and a second air outlet line 48. Air outlet line 46 is connected to an outlet tube 50 extending from waste filter 16 by a suitable fitting 52. Vacuum pressure may be controlled by a continuously variable air inlet valve 54. A pressure gauge 56 may also be provided to monitor the suction at the input to pump 22. The exhaust air from pump 22 may be exhausted to the atmosphere through a final filter/muffler 58.

Figure 2:
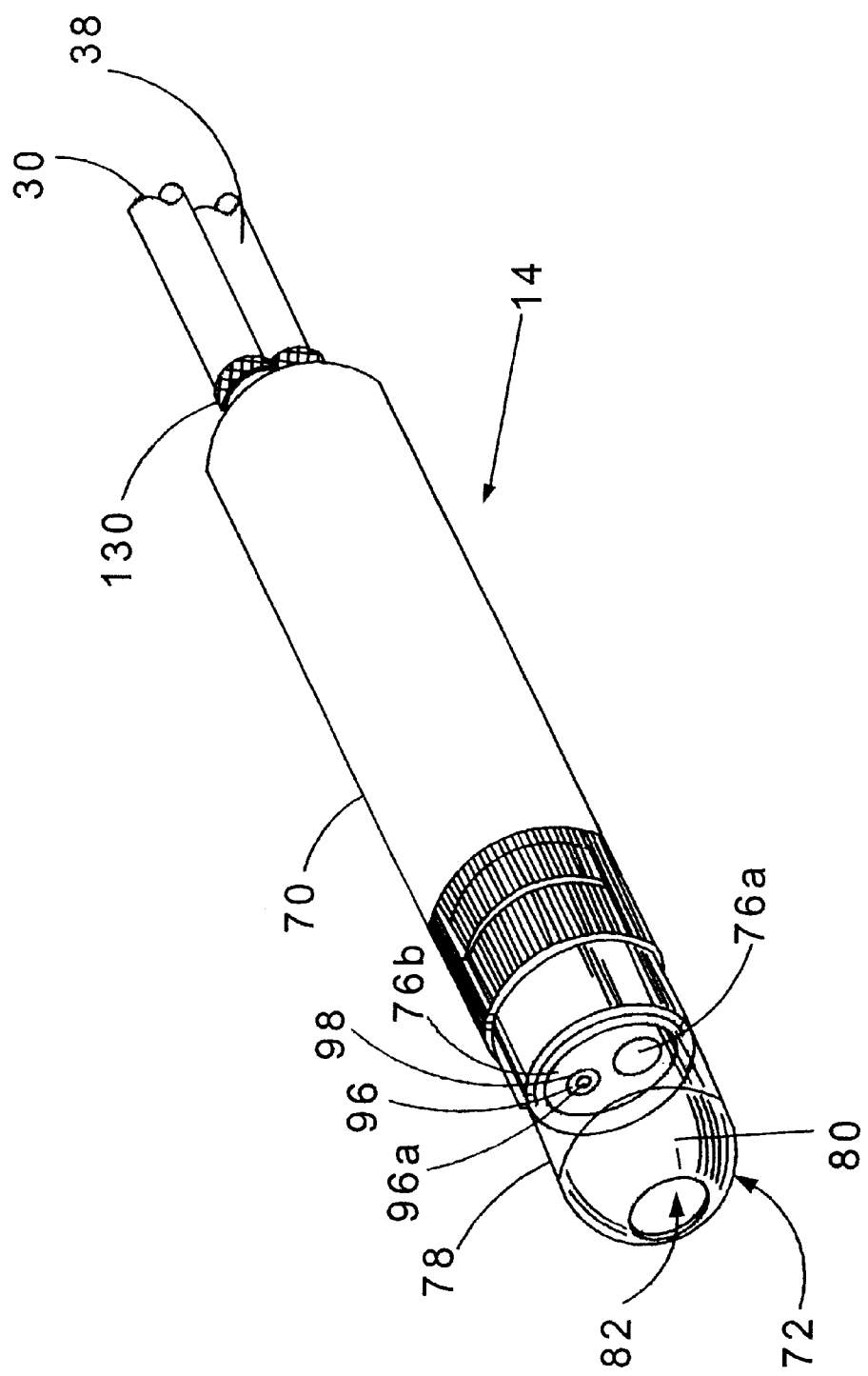
FIG. 2 is a perspective view of a novel handpiece as described in the present invention.

As illustrated in FIGS. 1–3, handpiece 14 is comprised of a cylindrical body 70 and a threadedly attached disposable tip 72. An inlet channel 74 extending through body portion 70 provides an inlet path for abrasive particles into tip 72, and a waste removal channel 76 extending through body portion 70 with an inlet opening 76a in face 76b of body 70 provides a waste disposal path for spent particles and abraded skin out of tip 72.

Removable tip 72 is formed of polycarbonate or other suitable plastic material and is comprised of a hollow cylindrical portion 78 and a curved end portion 80 which may be hemispheric, parabolic or the like. An axially located treatment orifice 82 at the end of tip 72 provides access by the stream of abrasive particles to the portion of the skin to be abraded. The diameter of orifice 82 is not critical, but good results are achieved with a diameter in the range of 0.25 to 0.375 in. (0.635–0.953 cm.)

Handpiece body 70 may be formed Teflon® or other suitable plastic and may be molded or machined to the required shape. Alternatively, handpiece body 70 may be comprised of stainless steel. The outside dimensions of handpiece 14 are not critical, but good results in terms of operator comfort and convenience are achieved with a handpiece having an overall length of less than 3 inches (7.62 cm.), e.g., 2.25 inches (5.715 cm.), and a diameter of less than 1.0 inch (2.54 cm.), e.g., 0.875 inch (2.22.25).

The diameters of channels 74 and 76 are also not critical, but must be sufficiently large to provide adequate particle flow with a vacuum pump 22 of reasonable capacity and power. It has also been found that the diameter of waste removal channel 76 should be larger than article supply channel 74. This helps promote rapid removal of spent abrasive particles and abraded skin, especially if the vacuum inside tip 72 is broken due to loss of contact of treatment orifice 82 with the skin surface. At the same time, if channels 74 and 76 are too large, the diameter of handpiece 14 must be increased, with consequent loss of maneuverablity and operator comfort. Given the foregoing considerations, it has been found that good results may be achieved if channels 74 and 76 are respectively 0.11 in. (2.794 mm.) and 0.08 in. (2.03 mm.) in diameter.

Handpiece body 70 is threadedly connected to tip 72 by external threads 84 that engage with complementary internal threads 86 on cylindrical portion 78 of tip 72. An O-ring seal 88 is provided at the base of threaded portion 84 and engages with an unthreaded skirt portion 90 at the end of tip 72.

As previously noted, treatment orifice 82 is preferably located axially at the end of tip 72. It has been found, however, that tissue removal is most effectively performed if the stream of abrasive particles is aimed directly at treatment orifice 82. Since channels 74 and 76 are laterally offset from the central axis of handpiece body 70, to direct the incoming particle stream into orifice 82, inlet channel 74 is oriented at a small angular offset from the longitudinal axis of handpiece body 70. For a handpiece and tip having the dimensions indicated above, it has been found that the offset angle θ, as illustrated in FIG. 3 is advantageously in the range of 3–4 degrees.

Alternatively, as illustrated in FIG. 4, instead of angling the entire length of channel 74, the upstream end 92 is oriented parallel to waste removal channel 76, and only the downstream discharge end 94 of channel 74 is angled.

It will, of course, be understood that the value of offset angle θ will depend on the particular dimensions of handpiece 14 and tip 72, the important consideration being that the particle stream impinge, as nearly as possible, in the center of treatment orifice 82.

In either the configuration of FIG. 3 or FIG. 4, an abrasion-resistant nozzle insert 96, fitted in a counter-bore 98 at the outlet end of supply channel 74, may be provided, as illustrated in FIG. 3. The abrasive particle stream thus exits toward treatment orifice 82 through opening 96a.

Microdermal abrasion unit 10 is preferably constructed with its major parts as an integrated unit. Thus, supply container 12, waste filter 16, tertiary in-line filter 20, vacuum pump 22, and the various ancillary parts are all preferably mounted in a single cabinet (not shown). Waste filter 16 and supply container 12 are preferably positioned for easy access and to facilitate removal as explained below.

Figure 6:
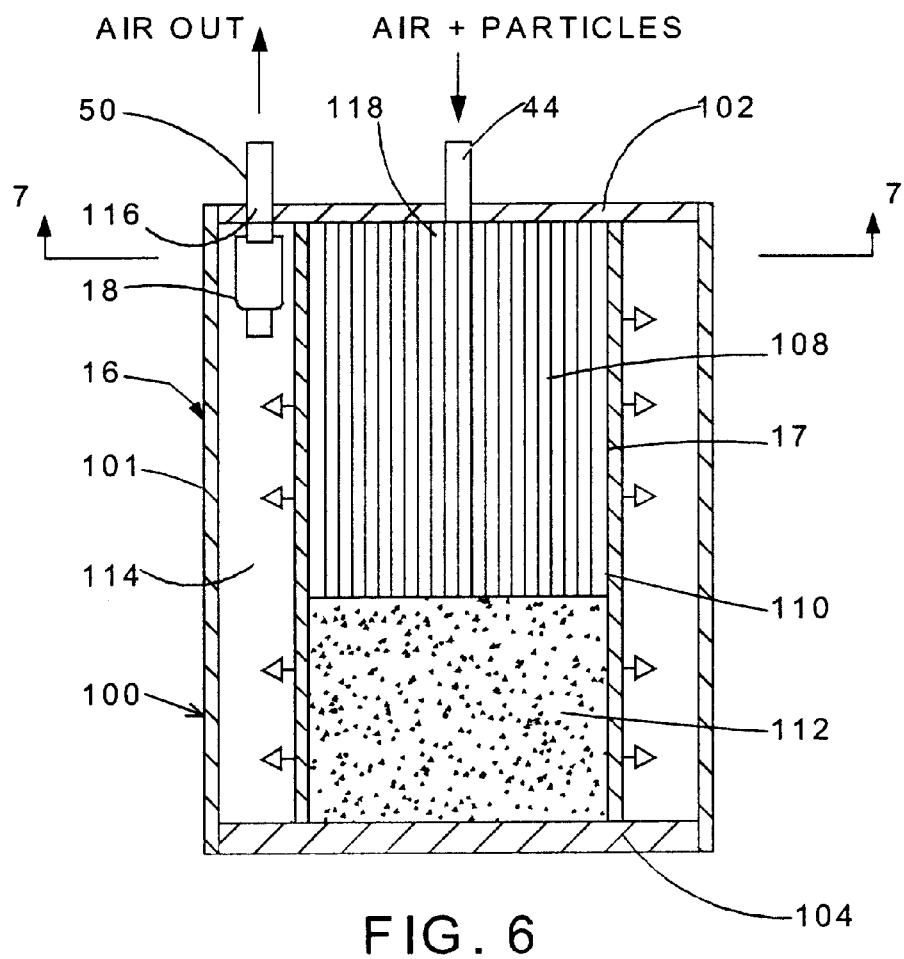
FIG. 6 is vertical sectional view of a disposable waste filter as described in the invention.
Figure 7:
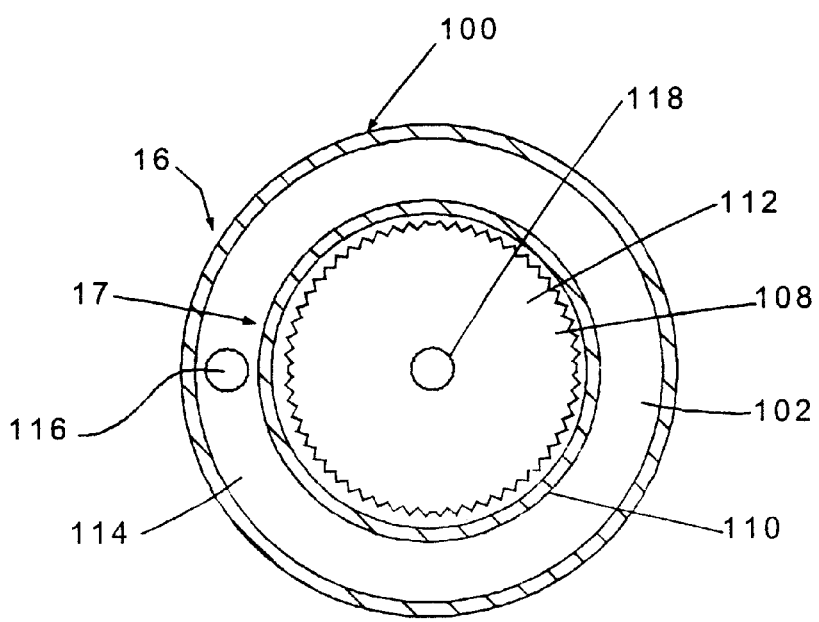
FIG. 7 is a cross-sectional view taken along line 7—7 in FIG. 6.

Referring to FIGS. 6 and 7, waste filter 16 is comprised of a cylindrical outer container 100 having a tubular body 101 permanently attached to top and bottom end caps 102 and 104. These may be comprised of metal, plastic or heavy cardboard tube. Within outer container 100 is primary filter 17. This may be cylindrical in form and comprised of a pleated inner portion 108 overwrapped with a flat filter paper portion 110. Alternatively, filter element 108 may be formed of a single layer, having either a pleated structure or a flat tubular structure. Filter element 108 is selected to ensure trapping of the 120 micron sized abrasive particles and the abraded tissue.

Filter element 108 defines a boundary between a central volume 112 enclosed thereby and an exterior generally annular shaped sealed volume 114 between the filter element and the interior of outer container 100.

Filter element 17 is fixed in place by cementing it to the top and bottom end caps 102 and 104, using a potting compound or the like, before outer container 100 is assembled. Top end cap 102 has openings 116 and 118 which receive air outlet tube 50 and waste inlet tube 44 sealingly connected therein. Tubes 50 and 44 may be flexible plastic tubes with O.D.'s of ⅜ and ¼ inch respectively.

Tube 50 extends through opening 116, and is connected at its end to secondary filter 18 which helps assure that there will be no venting of the waste material accumulated within waste filter 16, even if primary filter 17 ruptures for some reason. The illustrated construction also permits disposal of secondary filter 18 without risk of exposure to the waste material.

Since waste filter 16 is a unitary structure, it is conveniently removable, and disposable in one piece by disconnection of tubes 50 and 44 respectively from in-line filter 20 and output channel 76 in handpiece 14. Tubes 44 and 50 are advantageously long enough to be connected together as by a fitting 42 which fits into the end of tube 50 to completely seal the container for disposal.

It will be understood by those skilled in the art, however, that other forms of waste filters which permit disposal without exposure to the accumulated waste material may also be employed within the scope of this invention.

Referring again to FIG. 3, a small control opening 120 is provided in tip 72. This can be closed by the operator's finger to increase the vacuum and thereby produce a more forceful stream of abrasive particles against the skin being abraded when required without adjustment of valve 54 (see FIG. 1).

As will be appreciated, the same result can be obtained by placing an opening in handpiece body 70 (not shown) in communication with the interior of either inlet channel 74 or waste removal channel 76.

Referring to FIGS. 3 and 5, the upstream ends of channels 74 and 76 are internally tapered at 122 and 124 to receive tapered end portions of couplers 32 and 40. Coupler 32, illustrated in FIG. 5, is comprised of a pin 126 having a tapered end portion 128 adapted to fit into tapered end 122 of channel 74, a flange 130 and a cylindrical rear body portion 132 taped at its end 134, and adapted to fit into particle supply tube 30. Flange 130 provides a shoulder against which the end of tube 30 rests when assembled. (As will be understood, tube 30 may be heated before insertion of pin 126 so that the tube contracts around rear portion 132, thereby ensuring a tight fit. Coupler 40 is similarly constructed.

As will be understood by those skilled in the art, such a tapered connection (known as a Morse taper) provides a reliable connection which can be easily made and released even under substantial internal pressure simply by twisting plug 126. The periphery of flange 130 may be knurled at 136 to facilitate grasping for this purpose. The resulting connections are secure, but may easily be released by twisting the plug with two fingers. No tools are needed, and enlargement of the diameter of handpiece 14 to allow manipulation of the couplings is unnecessary.

It should also be understood that tapered fittings as described above may be used for other parts herein which must be connected and disconnected, such as the connections between waste filter 16 and tubes 38 and 46, the connection between vacuum pump 22 and tube 48, etc.

Two factors which have been found to be important in achieving satisfactory operation are the rate and uniformity of particle flow past treatment orifice 82 in handpiece 14. As will be appreciated, maximum particle flow rate depends in part on the capacity of vacuum pump 22. It has been found that effective treatment can be achieved in a practical configuration using a ¼ to ½ horsepower vacuum pump providing 90–98 KPA.

Uniformity of particle flow has been found to be related to the geometry of the structure of the particle flow path. This can produce rather complex effects, which in the extreme, can cause serious and frequent clogging of particle flow paths. It has been found, however, that such effects can be minimized by controlled mixing of air and particles before the particles are transported to handpiece 14. This may be done quite conveniently at supply container 12 using any of the embodiments described below. As a result, particle flow may be made substantially uniform, and clogging largely eliminated.

Figure 9:
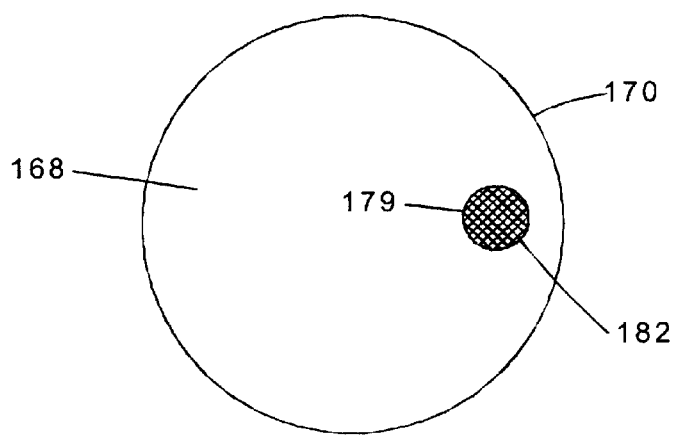
FIG. 9 is a top view of the particle supply container illustrated in FIG. 8.
Figure 8:
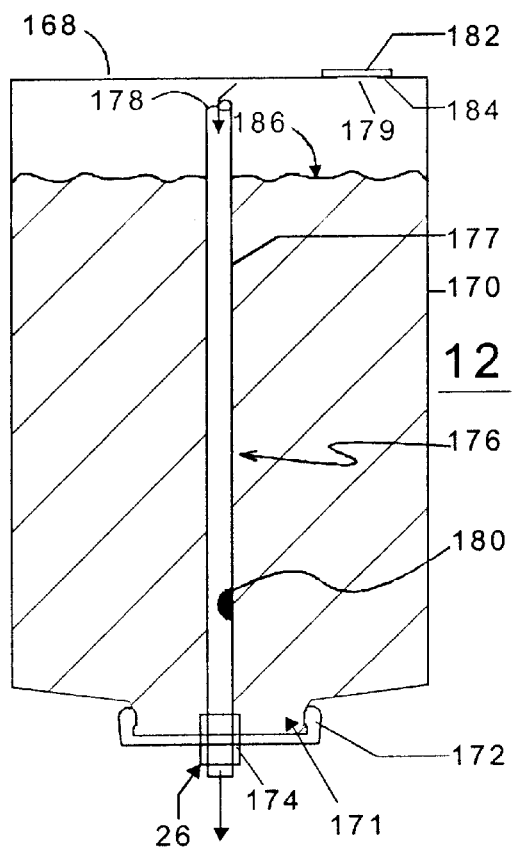
FIG. 8 is a side elevation of a first embodiment of novel pre-filled disposable particle supply container as described in the invention.
Figure 10:
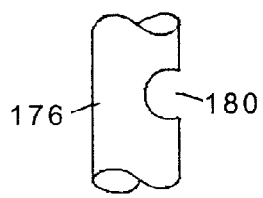
FIG. 10 is an enlarged view of a portion of the aeration tube of the supply container of FIG. 8 showing the particle inlet opening.

FIGS. 8–10 illustrate a preferred embodiment for particle supply container 12. As shown, container 12 is comprised of an outer receptacle 170 having a top 168 and a bottom opening 171 sealed by a suitable closure such as an end cap 172, a first air inlet 179 and an aeration device generally denoted at 176.

In the illustrated embodiment, aeration device 176 is comprised of a mixing chamber in the form of a tube 177, a second air inlet 178 and a particle inlet device 180. Tube 177 extends vertically to a point adjacent to the top of receptacle 170. A second air inlet 178 at the top of tube 177 permits inflow of air for mixing with the abrasive particles as described below. The bottom of tube 177 communicates through an opening 174 in end cap 172 with outlet coupler 26, which, in turn, is connected by outlet tube 24 and Tee-connector 28 to particle supplied tube 30 (see FIG. 1).

Referring again to FIGS. 8–10, first air inlet 179 is provided in the top of receptacle 170 to vent the air space above the particle fill level 186 to the atmosphere. An air filter 182 is secured over air inlet 179, e.g., by gluing at its periphery 184 to receptacle top 168.

In use, a supply container 12 is pre-filled by a supplier with abrasive material leaving an air space 186 below the top 178 of mixing tube 176. As will be understood, this permits air to be drawn into the tube by the suction created by vacuum pump 22 (see FIG. 1). The prefilled container is installed by removing a shipping cap (not shown) from the end of tube 176 and fitting 26 is attached to the tube 24.

Still referring to FIGS. 8 and 10, particle inlet opening 180 near the bottom of mixing tube 176 permits abrasive particles to enter the tube under the force of gravity and to create an air-particle mixture which is then transported through supply tube 30 to hand-piece 14. By aerating the particles in this manner, clumping due to accumulation of moisture is prevented without the need for heaters to dry the particles or vibrations, as are sometimes employed.

The dimensions of air intake opening 179 and particle inlet opening 180 in mixing tube 176 are selected to provide the desired degree of aeration. Good results are achieved with an air intake opening 179 having an internal diameter in the range of 0.1 to 0.175 in. (0.445 cm.), and preferably 0.125 in (0.3175 cm.) an outside diameter for tube 176 of 0.25 in. (0.635 cm.) and a particle inlet opening having a diameter in the range of 0.063 to 0.090 in. (1.006–2.286 mm.), and preferably 0.080 in. (2.032 mm.).

Further adjustment of the aeration maybe achieved by use of valve 36 connected to leg 34 of Tee-connector 28. By opening valve 36, more air is introduced to supply tube 30, thus reducing the quantity of abrasive particles. This allows continuous and infinite adjustment of the particle flow rate.

In a practical application, the capacity of container 12 maybe 1–5 pounds (0.454–2.268 kg.). Particle size is not critical, but it has been found that good results are achieved using irregularly shaped aluminum oxide particles having a maximum dimension less than about 120 microns and with sharp irregular edges.

When the container is empty, it is removed and replaced by a new prefilled container. The shipping cap is reapplied to the end of tube 176 and the empty container is then discarded.

FIGS. 11–21 illustrate several alternative embodiments for supply container 12. The embodiment shown in FIG. 11 differs from the embodiment of FIGS. 8–10 in that mixing tube 176 extends through a fitting 188 in the upper wall 189 of receptacle 170. Air enters tube 176 through an opening 191. A protective cap 190 is provided over opening 191. No separate air inlet such as 179 (see FIG. 8) is needed, but an air outlet hole 192 is provided near the top of tube 176 to vent air space 186 to the atmosphere. As will be understood, this is necessary to permit the particles to be drawn into particle supply opening 180 in tube 176.

Figure 11:
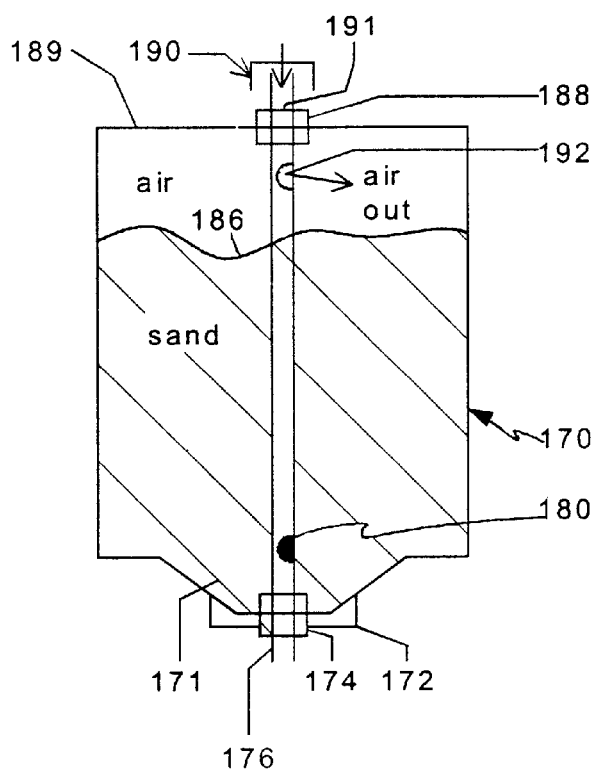
FIG. 11 is a side elevation of a second embodiment of the novel particle supply container as described in the invention.
Figure 12:
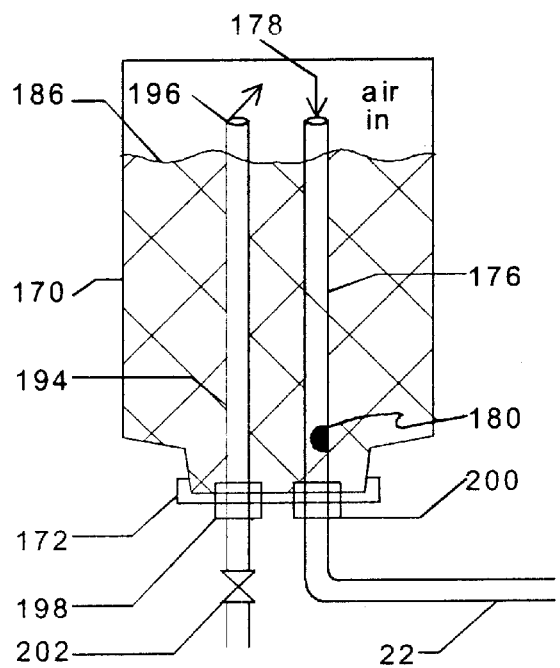
FIG. 12 is a side elevation of a third embodiment of the novel particle supply container as described in the invention.

The embodiment shown in FIG. 12 differs from that of FIG. 11 in that a separate air supply tube 194 is provided. Tube 194 is mounted in a fitting 198 in receptacle end closure 172, extends upwardly within receptacle 170 to a point above particle fill level 186 and terminates in an opening 196. Air enters tube 176 at its open top 178 and mixes with particles entering at inlet opening 180. Tube 176 terminates at a fitting 200 in closure 172, where it may be connected directly to particle supply tube 22 (see FIG. 1). Tee-coupler 28 and air valve 36 shown in FIG. 1 are not used. Instead, an in-line valve 202 in air intake tube 194 is provided to adjust air flow.

The embodiment of FIGS. 13 and 14 employs a separate particle inlet tube 204 which extends through an opening 180 in a mixing tube 176. Inlet tube 204 is positioned at an angle, e.g., 45°, so particles entering at upper opening 206 are gravity fed through lower opening 208 and are mixed with the air stream in outlet tube 176.

In the embodiment of FIGS. 15–17, the mixing chamber and the outlet device are combined. Air is provided from above, as in the previously described embodiments, through a vertically extending tube 210. Tube 210 is connected at its bottom end to a funnel 212 which terminates in a spout 214, the latter being connected to outlet tube 24 (see FIG. 1).

Abrasive particles are gravity-fed into spout 214 by a particle feed device generally denoted at 216, which is comprised of a circular trough that surrounds tube 210. Trough 216 is open at the top and is comprised of a side wall 219 and an annular bottom plate 222. Outlet tubes 220 connected to openings 224 in trough bottom plate 222 feed into spout 214 through openings 226.

As will be understood, the constructions shown in FIGS. 13–14 and FIGS. 15–17 may be used instead of the tubular mixing chambers and particle inlet devices in any of the embodiments shown in FIGS. 8–12.

In the embodiment illustrated in FIGS. 18 and 19, a tubular mixing chamber 230 is attached to the bottom 232 of receptacle 170. Spaced holes 234 in tube 230 communicate with aligned holes 236 in receptacle bottom 232 to permit a particle inlet. Alternatively, holes 234 may communicate with the interior of receptacle 170 through a slot in receptacle bottom 232 (not shown). Air is supplied through an air inlet 236 at one end of tube 230 and mixes with particles which are gravity fed through holes 234. The aerated mixture exits through an outlet device 238, which may be connected directly particle supply line 30. The air supply at inlet 236 and accordingly particle volume, may be controlled by an air valve (not shown).

A variant of the embodiment of FIGS. 18–19 is shown in FIGS. 20 and 21. Here, a cylindrical mixing chamber 240 is formed at the bottom of receptacle 170 by a horizontal dividing wall 242, including a plurality of perforations 246 by which the particles are gravity fed into mixing chamber 240. As in the embodiment of FIGS. 18–19, air is supplied at an inlet 248 through a valve (not shown) and the aerated mixture exits through an outlet device 250.

In summary, the present invention provides improvements in the art of microdermal abrasion including continuous variability of the particle flow rate and substantial elimination of shutdown due to clogging of the particle flow tubes, as well as improved uniformity of particle flow.

In addition, the present invention provides a handpiece and input channel which direct the flow of abrasive particles toward substantially the center of the opening in the tip, thereby improving the performance of the dermabrasion process.

Also, the Morse taper couplings employed as described in the present invention, particularly for connecting the particle supply and waste disposal lines to the handpiece, permit convenient connection and disconnection without tools, and allow the handpiece to be made small enough for convenient and comfortable use.

Moreover, the design of the supply container and waste filter permit disposal without risk of exposure to either clean or contaminated materials.

Although the present invention has been described in relation to particular embodiments thereof, many other variations and modifications and other uses will become apparent to those skilled in the art. Thus, other designs for the handpiece, the disposable supply container an the waste filter are possible. Similarly, the supply container need not be disposable. Instead it may be constructed in a manner permitting it to be refilled upon return to the supplier.

It is intended, therefore, that the scope of invention be limited not by the specific disclosure herein, but only by the appended claims.

What is claimed is:

1. A microdermal abrasion apparatus comprising:
   a supply container of abrasive particles, the container being installable and removable for disposal as an integral, substantially sealed unit;
   a handpiece for applying an input stream of abrasive particles to a skin surface through a particle supply channel and for removing a waste stream of particles and tissue abraded from the skin surface through a waste removal channel, the particle supply channel being connected to the supply container by a particle supply line to produce the input stream of abrasive particles;
   a waste filter connected to the waste removal channel in the handpiece by a waste disposal line, the waste filter being installable and removable for disposal as an integral, substantially sealed unit; the waste filter being comprised of:
   a waste inlet;
   an outer container;
   a filter element located in the outer container and connected to the waste inlet, the filter element providing a receptacle for spent abrasive particles and abraded tissue filtered from the incoming waste stream; and
   an air outlet for air filtered from the waste stream;
   a vacuum pump connected to the waste filter air outlet;
   an aerator which controllably mixes the abrasive particles with an air stream before delivery to the handpiece; and
   an adjustable air supply valve coupled to the aerator which controls the volume of abrasive particle flow through the particle supply line.

2. The apparatus described in claim 1, further comprising a second adjustable valve coupled to an inlet of the vacuum pump which controls the suction applied to the waste filter air outlet.

3. The apparatus described in claim 2, in which the second valve is continuously adjustable to infinitely vary the suction provided by the vacuum pump.

4. The apparatus described in claim 1, in which the air supply valve is continuously adjustable to infinitely vary the particle volume in the particle stream to the handpiece.

5. The apparatus described in claim 1, in which the aerator and the supply container are an integral unit, installable and removable for disposal as a single unit.

6. The apparatus as described in claim 1, in which the supply container is comprised of:
   a receptacle for abrasive particles, the receptacle having upper and lower ends;
   a first air inlet that provides a source of air at the upper end of the receptacle; and
   an outlet device in which the aeration device is comprised of:
   a mixing chamber communicating with the outlet device;
   a second air inlet opening in the mixing chamber; and
   a particle inlet device for entry of abrasive particles into the mixing chamber under the force of gravity;
   the aeration device being operative in response to suction applied to the outlet device to provide an aerated stream of abrasive particles.

7. The apparatus described in claim 6, in which the first air inlet comprises a vent in the upper end of the receptacle and an air filter which covers the vent.

8. The apparatus supply container described in claim 7, in which:
   the mixing chamber is comprised of a tube extending vertically in the receptacle;
   the second air inlet is comprised of an opening at an upper end of the tube in communication with the vented area at the upper end of the receptacle;
   the outlet device is comprised of a coupler in communication with an opening at a lower end of the tube, the coupler being connected to the particle supply line; and
   the particle inlet device is comprised of a feed opening in the wall of the tube intermediate the second air inlet and the opening at the lower end of the tube.

9. The apparatus described in claim 8, in which the particle inlet device is comprised of a feed tube having a first open end in communication with the feed opening in the wall of the tube, and a second open end in communication with the interior of the receptacle.

10. The apparatus described in claim 9, in which the first opening is disposed substantially vertically and the second opening is disposed substantially horizontally.

11. The apparatus described in claim 6, in which:
    the mixing chamber is comprised of a tube extending vertically in the receptacle, with an upper end thereof projecting through an opening in the upper end of the receptacle;
    the first air inlet is comprised of a vent opening adjacent to the upper end of the tube;
    the second air inlet is comprised of an opening in the projecting upper end or the tube;
    the outlet device is comprised of a coupler in communication with an opening at a lower end of the tube, the coupler being connected to the particle supply line; and
    the particle inlet device is comprised of a feed opening in the wall of the tube intermediate the second air inlet and the opening at the lower end of the tube.

12. The apparatus described in claim 6, in which:
    the first air inlet is comprised of a first tube having an opening at a first end thereof located adjacent to the upper end of the receptacle, and having an opening at a second end thereof exposed to the atmosphere:
    the mixing chamber is comprised of a second tube extending vertically in the receptacle, with an opening at the upper end thereof comprising the second air inlet;

the outlet device is comprised of a coupler in communication with an opening at a lower end of the tube, the coupler being connected to the particle supply line; and the particle inlet device is comprised of a feed opening in the wall of the tube intermediate the second air inlet and the opening at the lower end of the tube.

13. The apparatus described in claim 6, in which the mixing chamber is comprised of:

a tube extending vertically in the receptacle and having an opening at an upper end thereof comprising the second air inlet;

the outlet device is comprised of a funnel at a lower end of the tube, the funnel including a spout portion at the bottom thereof, the spout portion being connected to the particle supply line; and the particle feed device is comprised of a feed tube having a first open end in communication with an opening in the funnel, and a second open end above the first open end in communication with the interior of the receptacle.

14. The apparatus described in claim 6, in which the mixing chamber is comprised of:

a tube extending horizontally at the bottom of the receptacle;

the second air inlet is comprised of a first opening at one end of the tube;

the outlet device is comprised of a coupler in communication with an opening at a lower end of the tube, the coupler being connected to the particle supply line; and the particle feed device is comprised of a feed opening facing upwardly in the wall of the tube.

15. The apparatus described in claim 14, in which the tube extends along an outer surface of the bottom of the receptacle, and in which the particle feed device is further comprised of an opening in the bottom of the receptacle aligned with the feed opening.

16. The apparatus described in claim 14, in which the tube extends along an outer surface of the bottom of the receptacle, and in which the particle feed device is comprised of a plurality of third openings in the tube and a plurality of fourth openings in the bottom of the receptacle aligned respectively with the third openings.

17. The apparatus described in claim 6, in which:

the mixing chamber is comprised of a portion of the receptacle separated from a main portion thereof by a substantially horizontal dividing wall portion;

the second air inlet is comprised of a first opening in a vertical wall of the mixing chamber;

the outlet device is comprised of a coupler in communication with an opening at a lower end of the tube, the coupler being connected to the particle supply line; and the particle feed device is comprised of a plurality of third openings in the dividing wall.

18. The apparatus described in claim 1, in which the particle supply line and the waste disposal line are each connected to the handpiece by a coupler including a Morris taper.

19. The apparatus described in claim 1, in which an upstream ends of the particle supply and waste removal channels in the handpiece are internally tapered to receive externally tapered fittings respectively attached to the particle supply and waste removal lines.

20. The apparatus described in claim 1, in which the handpiece is comprised of a body portion having the particle supply and waste disposal channels therein and a removable tip having a treatment orifice therein through which the stream of abrasive particles is applied to the skin, the treatment orifice being positioned along a longitudinal axis of the handpiece, the longitudinal axis, and the particle supply channel being so oriented that the particles are directed substantially toward the center of the treatment orifice.

21. A handpiece for a microdermal abrasion apparatus comprising:

a body portion elongated along a central axis;

first and second channels extending substantially lengthwise in the body portion, and having respective upstream and downstream ends;

a disposable tip portion connected to the body portion and having a treatment orifice at one end coaxial with the central axis;

the first channel being connectable at its upstream end to a supply line for abrasive particles;

the downstream end of the first channel being located off the central axis, and oriented so that a stream of abrasive particles exiting therefrom is directed substantially toward the center of the treatment orifice;

the downstream end of the second channel being connectable through a waste disposal line to a source of suction;

the upstream end of the second channel being positioned to remove spent abrasive particles and abraded skin from the handpiece tip upon application of suction through the waste disposal line.

22. The handpiece described in claim 21, wherein the first channel is substantially linear and is oriented at an oblique angle with respect to the central axis.

23. The handpiece described in claim 21, wherein an upstream portion of the first channel is oriented substantially parallel to the central axis, and a downstream portion of the first channel is oriented at an oblique angle with respect to the central axis.

24. The handpiece as described in claim 23, wherein the oblique angle is approximately four degrees.

25. The handpiece described in claim 21, wherein the tip portion is threadedly connected to the body portion.

26. The handpiece described in claim 21, wherein the upstream ends of each first and second channels are tapered to receive fittings having complementary tapers.

27. A method for microdermal abrasion employing apparatus including a supply container for abrasive particles, a treatment handpiece, a waste filter and a pump providing a source of operating pressure, the method comprising:

obtaining a pre-filled substantially sealed container of abrasive particles from a supplier;

withdrawing a stream of abrasive particles from the container through a supply line;

directing the stream of abrasive particles from the supply line through a supply channel in a handpiece, substantially toward the center of a treatment orifice at one end of the handpiece, the treatment orifice being substantially coaxial with a central axis of the handpiece;

placing the treatment orifice in contact with a portion of skin to be abraded;

withdrawing a waste stream of abrasive particles and abraded skin through a waste disposal channel in the handpiece;

directing the waste stream to a waste filter having an integral outer container, and a filter element sealingly contained within the outer container, filtering the waste stream through the waste filter;

withdrawing a filtered air stream from the interior of the waste filter;

disposing of an empty supply container without disassembly and in substantially sealed condition; and disposing of the waste filter when necessary without disassembly of the outer container.

28. The method described in claim 27, further including changing the pressure of the particle stream within the handpiece by manually closing an outlet opening therein while otherwise manipulating the handpiece over the skin surface.

29. A method as described in claim 27, further including aerating the particle stream by introducing particles into a mixing chamber within the supply container and operating the pump to introduce air into the mixing chamber and to withdraw the aerated particle stream through an outlet.

30. A method as described in claim 29, further including adjusting the quantity of air introduced into the mixing chamber by a operation of a continuously adjustable valve.

31. The process as described in claim 27, wherein the operating pressure is provided by a vacuum pump, and further including operating a continuously adjustable valve to control the suction in the handpiece.

32. A particle supply container for a microdermal abrasion apparatus which employs a stream of particles to abrade a surface layer of skin, the particle supply container being installable and removable for disposal as an integral substantially sealed unit, and being comprised of:

a receptacle for abrasive particles, the receptacle having upper and lower ends;

a first air inlet that provides a source of air at the upper end of the receptacle; and an aeration device, the aeration device being comprised of:
  a mixing chamber;
  a second air inlet opening in the mixing chamber;
  a particle inlet device for entry of abrasive particles into the mixing chamber under the force of gravity; and
  an outlet device communicating with the mixing chamber;
  the aeration device being operative in response to suction being applied to the outlet device to provide an aerated stream of abrasive particles.

33. The particle supply container described in claim 32, further including an end cap that is sealingly attachable to one end of a receptacle which has been filled with a quantity of abrasive particles.

34. The particle supply container described in claim 32, in which the first air inlet comprises an opening in the upper end of the receptacle and an air filter which covers the opening.

35. The particle supply container described in claim 34, in which:

the mixing chamber is comprised of a tube extending vertically in the receptacle;

the second air inlet is comprised of an opening at an upper end of the tube in communication with the vented area at the upper end of the receptacle;

the outlet device is comprised of a coupler in communication with an opening at a lower end of the tube, the coupler being connectable to a particle supply tube; and the particle inlet device is comprised of a feed opening in the wall of the tube intermediate the second air inlet and the opening at the lower end of the tube.

36. The particle supply container described in claim 35, wherein the particle inlet device is comprised of a feed tube having a first open end in communication with the feed opening in the wall of the tube, and a second open end in communication with the interior of the receptacle.

37. The particle supply container described in claim 36, in which the first opening is disposed substantially vertically and the second opening is disposed substantially horizontally.

38. The particle supply container described in claim 32, in which:

the mixing chamber is comprised of a tube extending vertically in the receptacle, with an upper end thereof projecting through an opening in the upper end of the receptacle;

the first air inlet is comprised of a vent opening adjacent to the upper end of the tube;

the second air inlet is comprised of an opening in the projecting upper end or the tube;

the outlet device is comprised of a coupler in communication with an opening at a lower end of the tube, the coupler being connectable to a particle supply tube; and the particle inlet device is comprised of a feed opening in the wall of the tube intermediate the second air inlet and the opening at the lower end of the tube.

39. The particle supply container described in claim 32, in which:

the first air inlet is comprised of a first tube having an opening at a first end thereof located adjacent to the upper end of the receptacle, and having an opening at a second end thereof exposed to the atmosphere;

the mixing chamber is comprised of a second tube extending vertically in the receptacle, with an opening at the upper end thereof comprising the second air inlet;

the outlet device is comprised of a coupler in communication with an opening at a lower end of the tube, the coupler being connectable to a particle supply tube; and the particle inlet device is comprised of a feed opening in the wall of the tube intermediate the second air inlet and the opening at the lower end of the tube.

40. The particle supply container described in claim 32, in which the mixing chamber is comprised of:

a tube extending vertically in the receptacle and having an opening at an upper end thereof comprising the second air inlet;

the outlet device is comprised of a funnel at a lower end of the tube, the funnel including a spout portion at the bottom thereof, the spout portion being connectable to a particle supply line; and the particle feed device is comprised of a feed tube having a first open end in communication with an opening in the funnel, and a second open end above the first open end in communication with the interior of the receptacle.

41. The particle supply container described in claim 32, in which the mixing chamber is comprised of:

a tube extending horizontally at the bottom of the receptacle;

the second air inlet is comprised of a first opening at one end of the tube;

the outlet device is comprised of a coupler in communication with an opening at a lower end of the tube, the coupler being connectable to a particle supply tube; and the particle feed device is comprised of a feed opening facing upwardly in the wall of the tube.

42. The particle supply container described in claim 41, in which the tube extends along an outer surface of the bottom of the receptacle, and in which the particle feed device is further comprised of an opening in the bottom of the receptacle aligned with the feed opening.

43. The particle supply container described in claim 41, in which the tube extends along an outer surface of the bottom of the receptacle, and in which the particle feed device is comprised of a plurality of third openings in the tube and a plurality of fourth openings in the bottom of the receptacle aligned respectively with the third openings.

44. The particle supply container described in claim 32, in which:
the mixing chamber is comprised of a portion of the receptacle separated from a main portion thereof by a substantially horizontal dividing wall portion;
the second air inlet is comprised of a first opening in a vertical wall of the mixing chamber;
the outlet device is comprised of a coupler in communication with an opening at a lower end of the tube, the coupler being connectable to a particle supply tube; and
the particle feed device is comprised of a plurality of third openings in the dividing wall.

45. A particle supply container for a microdermal abrasion apparatus which employs a stream of particles to abrade a surface layer of skin, the particle supply container being installable and removable for disposal as an integral substantially sealed unit, and being comprised of:
a receptacle containing a quantity of abrasive particles, the quantity of abrasive particles being sufficient to substantially fill the receptacle except for an air space at an upper end thereof;
a first air inlet that provides a source of air at the upper end of the receptacle; and
an aeration device, the aeration device being comprised of:
a mixing chamber;
a second air inlet opening in the mixing chamber;
a particle inlet device for entry of abrasive particles into the mixing chamber under the force of gravity; and
an outlet device communicating with the mixing chamber, the aeration device being operative in response to suction being applied to the outlet device to provide an aerated stream of abrasive particles.

46. The particle supply container described in claim 45, further including an end cap that is sealingly attached to one end of a receptacle after the receptacle has been filled with the quantity of abrasive particles.

47. The particle supply container described in claim 45, in which the first air inlet comprises a vent in the upper end of the receptacle and an air filter which covers the vent.

48. The particle supply container described in claim 47, in which:
the mixing chamber is comprised of a tube extending vertically in the receptacle;
the second air inlet is comprised of an opening at an upper end of the tube in communication with the air space at the upper end of the receptacle;
the outlet device is comprised of a coupler in communication with an opening at a lower end of the tube, the coupler being connectable to a particle supply tube; and
the particle inlet device is comprised of a feed opening in the wall of the tube intermediate the second air inlet and the opening at the lower end of the tube.

49. The particle supply container described in claim 48, wherein the particle inlet device is comprised of a feed tube having a first open end in communication with the feed opening in the wall of the tube, and a second open end in communication with the interior of the receptacle.

50. The particle supply container described in claim 49, in which the first opening is disposed substantially vertically and the second opening is disposed substantially horizontally.

51. The particle supply container described in claim 45, in which:
the mixing chamber is comprised of a tube extending vertically in the receptacle, with an upper end thereof projecting through an opening in the upper end of the receptacle;
the first air inlet is comprised of a vent opening in the tube adjacent to the upper end thereof,
the first air inlet being in communication with the air space at the upper end of the receptacle;
the second air inlet is comprised of an opening in the projecting upper end or the tube;
the outlet device is comprised of a coupler in communication with an opening at a lower end of the tube, the coupler being connectable to a particle supply tube; and
the particle inlet device is comprised of a feed opening in the wall of the tube intermediate the second air inlet and the opening at the lower end of the tube.

52. The particle supply container described in claim 45, in which:
the first air inlet is comprised of a first tube having an opening at a first end thereof in communication with the air space at the upper end of the receptacle, and having an opening at a second end thereof exposed to the atmosphere;
the mixing chamber is comprised of a second tube extending vertically in the receptacle, with an opening communicating with the air space at the upper end of the receptacle comprising the second air inlet;
the outlet device is comprised of a coupler in communication with an opening at a lower end of the tube, the coupler being connectable to a particle supply tube; and
the particle inlet device is comprised of a feed opening in the wall of the tube intermediate the second air inlet and the opening at the lower end of the tube.

53. The particle supply container described in claim 45, in which the mixing chamber is comprised of:
a tube extending vertically in the receptacle and having an opening communicating with the air space at the upper end of the receptacle comprising the second air inlet;
the outlet device is comprised of a funnel at a lower end of the tube, the funnel including a spout portion at the bottom thereof, the spout portion being connectable to a particle supply line; and
the particle feed device is comprised of a feed tube having a first open end in communication with an opening in the funnel, and a second open end above the first open end in communication with the interior of the receptacle.

54. The particle supply container described in claim 45, in which the mixing chamber is comprised of:
a tube extending horizontally at the bottom of the receptacle;
the second air inlet is comprised of a first opening at one end of the tube;
the outlet device is comprised of a coupler in communication with an opening at an end of the tube opposite the first opening, the coupler being connectable to a particle supply tube; and the particle feed device comprises a feed opening facing upwardly in the wall of the tube.

55. The particle supply container described in claim 54, in which the tube extends along an outer surface of the bottom of the receptacle, and in which the particle feed device is further comprised of an opening in the bottom of the receptacle aligned with the feed opening.

56. The particle supply container described in claim 54, in which the tube extends along an outer surface of the bottom of the receptacle, and in which the particle feed device is comprised of a plurality of third openings in the tube and a plurality of fourth openings in the bottom of the receptacle aligned respectively with the third openings.

57. The particle supply container described in claim 45, in which:

the mixing chamber is comprised of a portion of the receptacle separated from a main portion thereof by a substantially horizontal dividing wall portion;

the second air inlet is comprised of a first opening in a vertical wall of the mixing chamber;

the outlet device is comprised of a second opening diametrically opposite to the first opening and a fitting connectable to a particle supply line; and the particle feed device is comprised of a plurality of third openings in the dividing wall.

* * * * *